US006308094B1

(12) United States Patent
Shusterman et al.

(10) Patent No.: US 6,308,094 B1
(45) Date of Patent: *Oct. 23, 2001

(54) SYSTEM FOR PREDICTION OF CARDIAC ARRHYTHMIAS

(75) Inventors: Vladimir Shusterman; Benhur Aysin; Ilan Grave, all of Pittsburgh; Luis F. Chaparro, Monroeville; Kelley P. Anderson, Sewickley, all of PA (US)

(73) Assignee: University of Pittsburgh of the Commonwealth System of Higher Education, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/376,027

(22) Filed: Aug. 17, 1999

Related U.S. Application Data

(63) Continuation-in-part of application No. 09/067,586, filed on Apr. 28, 1998, now Pat. No. 5,967,995.

(51) Int. Cl.[7] .................................................. A61N 5/0468
(52) U.S. Cl. .............................................................. 600/516
(58) Field of Search ..................................... 600/515–518

(56) References Cited

U.S. PATENT DOCUMENTS

| | | |
|---|---|---|
| 4,492,235 | 1/1985 | Sitrick . |
| 4,777,960 | 10/1988 | Berger et al. . |
| 4,791,936 | 12/1988 | Snell et al. . |
| 4,802,491 | 2/1989 | Cohen et al. . |
| 4,960,129 | 10/1990 | dePaola et al. . |
| 5,042,497 | 8/1991 | Shapland . |
| 5,090,418 | 2/1992 | Squires et al. . |
| 5,215,099 | 6/1993 | Haberl et al. . |
| 5,291,400 | 3/1994 | Gilham . |
| 5,447,519 | 9/1995 | Peterson . |
| 5,560,370 | 10/1996 | Verrier et al. . |
| 5,628,326 | 5/1997 | Arand et al. . |
| 5,655,540 | 8/1997 | Seegobin . |
| 5,755,671 | 5/1998 | Albrecht et al. . |
| 5,967,995 | * 10/1999 | Shusterman et al. ................ 600/516 |

OTHER PUBLICATIONS

Laguna et al., "Karhunen–Loeve Transform as a Tool to Analyze the ST–Segment", *Journal of Electrocardiology*, pp. 41–49, vol. 29 Supplement.

Fukunaga et al., "Application of the Karhunen–Loeve Expansion to Feature Selection and Ordering", IEEE *Transactions on Computers*, Apr. 1970, pp. 311–318.

(List continued on next page.)

*Primary Examiner*—William E. Kamm
(74) *Attorney, Agent, or Firm*—David W. Brownlee; Eckert Seamans Cherin & Mellott, LLC

(57) ABSTRACT

A medical device and method for predicting cardiac arrhythmias, by gathering electrocardiographic data such as intervals between heart beats (RR-series) or other signal, mathematically decomposing or compressing the signal into several elements or components that contain the most significant information and tracking the changes in the several elements. The signal may be divided into time windows, and the signals decomposed into a plurality of coefficients or components such as Karhunen Loeve Transformation (KLT) coefficients that are predictive of the occurrence of a cardiac arrhythmia. The electrocardiographic data may be generated real-time, on-line, or be prerecorded data.

25 Claims, 14 Drawing Sheets

OTHER PUBLICATIONS

Pratt et al., "Analysis of Ambulatory Electrocardiograms in 15 Patients During Spontaneous Ventricular Fibrillation With Special Reference to Preceding Arrhythmic Events", Nov. 1983, pp. 789–797, JACC vol. 2, No. 5.

Corr et al., "Mechanisms Controlling Cardiac Autonomic Function and Their Relation to Arrhythmogenesis", *The Heart and Cardiovascular System,* 1986, pp. 1343–1403.

Martin et al., "Heart Rate Variability and Sudden Death Secondary to Coronary Artery Disease During Ambulatory Electrocardiographic Monitoring", *The American Journal of Cardiology,* Jul. 1987, pp. 86–89, vol. 60.

Moody et al., "QRS Morphology Representation and Noise Estimation Using the Karhunen–Loeve Transform", *Computers in Technology,* 1990, pp. 269–272, IEEE Computer Society.

Degani et al., "Karhunen–Loeve Coding of ECG Signals", IEEE, 1991, pp. 395–398.

Skinner et al., "A reduction in the correlation dimension of heartbeat intervals precedes imminent ventricular fibrillation in human subjects", *American Heart Journal,* Mar. 1993, pp. 731–743, vol. 125, No. 3.

Bayly et al., "Predicting Patterns of Epicardial Potentials During Ventricular Fibrillation", IEEE *Transactions on Biomedical Engineering,* Sep. 1995, pp. 898–907, vol. 42, No. 9.

Makikallio et al., "Abnormalities in Beat to Beat Complexity of Heart Rate Dynamica in Patients With a Previous Myocardial Infarction", Oct. 1996, pp. 1005–1011, JACC vol. 28, No. 4.

Kleiger et al., "Ambulatory Monitoring—Sudden Death" (Abstract), Feb. 1984, p. 547, JACC vol. 3, No. 2.

Magid et al., "Diminished Heart Rate Variability in Sudden Cardiac Death", *Abstracts of the 58th Scientific Sessions,* p. III–241, Abstract No. 964.

* cited by examiner

SYSTEM FOR PREDICTION OF CARDIAC ARRHYTHMIAS

This Application is a C-I-P of Ser. No. 09/067,586 filed Apr. 28, 1998, Pat. No. 5,967,995.

FIELD OF THE INVENTION

This invention relates to the field of electrocardiography and more specifically to a method and apparatus for evaluating patients to predict the risk of a patient having a cardiac arrhythmia, including life-threatening cardiac arrhythmia (LTCA) and non life-threatening cardiac arrhythmias.

BACKGROUND OF THE INVENTION

Cardiac arrhythmias involve abnormal electrical conduction or automatic changes in heart rhythm. Arrhythmias may vary in severity from those that are mild and require no treatment to those that are catastrophic and life threatening. Most life-threatening arrhythmias involve ventrical fibrillations. Atrial fibrillations are usually not life-threatening.

Most cardiac rhythm monitoring is performed to prevent death due to life-threatening cardiac arrhythmias (LTCA). However, current technology provides little more than detection and recognition of LTCA after it has started. This leaves very little time to protect the individual from death; the rhythm must be terminated within minutes or permanent neurologic damage or death will occur.

Only one method is in common use to predict an impending LTCA, namely, the frequency and complexity of premature ventricular complexes (PVCs). Our research, and that of others, suggests this method is unreliable. In the majority of patients the changes in frequency or complexity of PVCs do not correspond to the periods that precede initiation of LTCA. This failure probably accounts for its lack of commercial development.

Our results and those of other investigators demonstrate that the changes in RR-series can be a more accurate predictor of imminent LTCA than PVCs. However, the complexity and variability of RR-changes in different patients and even in the same patient during different periods of monitoring obscured application of this method for prediction of LTCA. Previous studies were focused on the detection of a single type of changes in the RR-series and did not allow to identify both linear and nonlinear changes. This diminished the accuracy of analysis, and made the results applicable to a small proportion of patients.

Frequency components of the RR-series contain physiologically important information about the activity of autonomic nervous system which, in turn, plays a major role in the initiation of LTCA. However, the nonstationary character of the signal affects the accuracy of spectral techniques. To overcome this problem, analysis based on Fast Fourier transform (FFT) or autoregressive modeling is usually performed over short and relatively stationary parts of the signal. Another approach uses the wavelet transform to decompose the signal into predefined frequency elements. However, neither method allows reliable identification of the nonstationary frequency elements that exhibit changes before LTCA. The analysis of short time windows requires stationarity of each portion of the signal, whereas the RR-series exhibits pronounced changes preceding LTCA. The wavelet transform decomposes the signal into constant frequency ranges, while individual RR-signals have highly variable frequency content.

Methods in general use include simple heart rate detection and frequency and, in some cases, repetitiveness of premature ventricular complexes (PVCs). The heart rate detector is set at high and low thresholds by the operator, and an alarm sounds if these are exceeded. The more sophisticated instruments also alarm when target thresholds for PVC frequency are exceeded. These are simple, primitive, inaccurate and ineffective. There is no method for predicting LTCA, only detection once they are in progress. Moreover, specificity for detection of significant arrhythmias is poor.

The linear changes before LTCA in the majority of patients (80–90%) are not different from those during the arrhythmia-free periods. Because these changes are not specifically associated with LTCA, in the majority of patients they cannot be used for the short-term prediction of arrhythmias. Conventional heart rate variability analysis in the frequency domain has revealed a complex pattern of changes but fails to identify specific changes that might predict LTCA as well. Moreover, the standard time (mean and standard deviation) and frequency (power spectrum) domain representations of a signal do not reveal the nonlinear changes that precede LTCA.

In animals and a small group of patients nonlinear methods based on different measures of complexity and deterministic chaos reveal low-dimensional excursions in the heart beat dynamics several hours before LTCA. Using point correlation dimension it was shown that the dynamics of heart rate over 12–24 hours before LTCA (ventricular fibrillation) exhibited low dimensional excursions in patients with ventricular fibrillation compared to the patients with similar clinical characteristics but without LTCA or to normal subjects. Enhanced nonlinear beat-to-beat alterations were observed 1 hour before the onset of LTCA in Poincare plots.

However, those methods do not allow extraction of the pattern, the onset, individual characteristics and the time course of changes. RR-changes are highly variable in different subjects and even in the same subject over different periods of time.

There is a need for a system for on-line, real-time electrocardiographic evaluation of patients that provides improved ability to assess the likelihood of an occurrence of cardiac arrhythmias including life-threatening and non life-threatening arrhythmias. Reliable prediction of a potentially fatal event requires risk estimation to adjust treatment strategy.

SUMMARY OF THE INVENTION

This invention predicts the imminent occurrence of a cardiac arrhythmia and will provide warning of the impending arrhythmia and allow preventive or protective measures to be instituted earlier with less risk, greater effectiveness and lower cost. This invention decomposes on-line, real-time or off line electrocardiographic (ECG) data to provide a plurality of component signals for a series of time windows. The component signals for the time windows are compared with each other for signs indicating that an arrhythmia may occur. This invention includes mathematical compression or decomposition of a signal containing electrocardiographical data into a small number (2–10) of elements that contain the most significant information about the signal, and tracking the changes in these elements that represent individual alterations in the controlled variables. Tracking the changes in the elements is preferably done by dividing the signals into a series of time windows or time segments and identifying variations in the elements in successive time windows. An impending arrhythmia, such as an LTCA, is indicated by increased variances and/or changes in mean values in at least some of the elements of the signal 1–3 hours prior to the arrhythmia.

A preferred embodiment of this invention uses the pattern of beat-to-beat heart rate changes to predict an impending LTCA. More precisely, the preferred embodiment analyzes the series of intervals between heart beats, referred to as RR-series, and the pattern of changes in these intervals, i.e., RR variability (RRV).

The present invention is suitable for use in most cardiac rhythm monitoring equipment and devices in circumstances where there is any possibility of an arrhythmia. Specifically, this would include: 1) all cardiac rhythm monitoring devices used in hospitals (e.g., emergency room, intensive care unit, cardiac step-down unit, surgical intensive care units, operating and procedure rooms, recovery rooms); 2) cardiac rhythm monitoring devices used out-of-hospital (e.g., at patient's home or work, medical transportation); 3) automatic external defibrillators; 4) implantable cardioverter defibrillators; 5) pacemakers; and 6) other systems for diagnostic ECG processing and analysis.

A preferred embodiment of the present invention detects and estimates linear and nonlinear changes in RR-series to predict LTCA. This invention preferably uses Karhunen-Loeve Transform (KLT) to characterize an individual's RR-series, but other pattern recognition methods or signal processing methods can also be used. Any changes in the signal that deviate from the characteristic signal pattern are represented in the KLT-decomposition or other wavelet decomposition. The characteristics of the KLT-decomposition are obtained from the KLT-coefficients and eigenvectors.

The preferred embodiment of this invention determines the probability of LTCA by determining: 1) the magnitude of the changes using the time varying mean and variance of KLT-coefficients; and 2) the complexity of the changes by calculating the number of KLT-coefficients that exhibit simultaneous changes.

The invention provides information about the spectral characteristics of changing frequency elements. In the preferred embodiment, this is accomplished by the spectral analysis of the first eigenvectors that represent the signal with a low residual error, multiplication of their frequency representations by the corresponding coefficients in each of the time windows, and summing the products of the multiplications. The result of this procedure produces an approximate frequency representation (AFR) of the signal in each time window. Subtracting AFR preceding the time of changes in KLT-coefficients from AFR after that time produces the frequency characteristics of changes in RR-series. Because the basis functions are obtained from the statistics of the individual signal, they can be viewed as a set of band-pass filters with frequency bandwidths that depend on the signal content. In contrast to the nonstationary behavior of the RR-series, its eigenvectors are stationary which permits accurate spectral representations. Therefore, the method of this invention accurately identifies stationary and changing frequency elements and their spectral characteristics. The frequency content of the changes in RR-series makes it possible to infer the physiologic mechanisms underlying the electrical instability which, in turn, will indicate the most appropriate response necessary to prevent the LTCA.

Additional physiologic and predictive information is provided by the magnitude of changes in the RR-series which can be estimated by the magnitude of change in KLT-coefficients. This includes, but is not limited to, time varying mean and standard deviation of the KLT-coefficients.

Alternatively to the RR-series data, this invention may use other variables including ECG variables (e.g., QT interval), and physiologic variables (e.g., blood pressure, vasomotor tone). This would include signals obtained from internal (inside the body) or external sources. Internal sources would include: within a cardiac chamber (intracavitary), within a blood vessel (intravascular), in the myocardium or other organ, or tissue between cells (interstitial), in the myocardial or other organ cells (intracellular). External signals are those obtained at the skin surface or away from the body. The types of signals to which the invention would apply are 1) electrical (e.g., electrocardiographic, electro-encephalographic, electromyographic, electrodermographic, or electroneurographic); 2) pressure, force, tension, vibration or acceleration-related by means of various transducers including piezoelectric or strain-gauge generated (e.g., intracardiac, intravascular venous arterial, vasomotor or pulmonary pressure or force); 3) sonic, i.e., sound-wave derived (usually by reflection) to detect motion of structures internally or externally (e.g., cardiac contractility, vasomotor, cardiac dimensions); or 4) sonic using the Doppler effect to detect blood flow or pressure externally or internally (e.g., in coronary arteries, cerebral arteries, pulmonary arteries, aorta or peripheral vessels); 5) magnetic (e.g., cardiac, brain, or muscle); 6) temperature (e.g., intravascular, skin, breath); 7) optical (e.g., based on changing light, contrast, or color, by optical filters or by image subtraction technique, including colorometric-fiberoptical determinations of oxygen saturation of hemoglobin, voltage sensitive dyes, lasers, and infrared devices); 8) chemical (e.g., intravascular, interstitial or intracellular sensor-determination of ionic activity, pH or chemical concentration such as potassium ion activity, drug concentrations, or expired air gasses.

This invention can be adjusted to particular clinical settings to optimize prediction of LTCA. For example, the optimal predictive indices during an acute myocardial infarction are different than those related to chronic recurrent ventricular tachycardia.

This invention detects the period of instability during which the risk of LTCA is high 1–3 hours before the event and provides a window of opportunity for the prevention of LTCA. The time of onset of this period is determined by the combined changes in three or more using pattern recognition methods such as KLT-coefficients.

The above and other objects and advantages of the invention will be more fully understood and appreciated by reference to the following description and attached drawings.

BRIEF DESCRIPTION OF THE DRAWINGS

A full understanding of the invention can be gained from the following description of the preferred embodiments when read in conjunction with the accompanying drawings in which.

DESCRIPTION OF THE PREFERRED EMBODIMENTS

Figure 1:
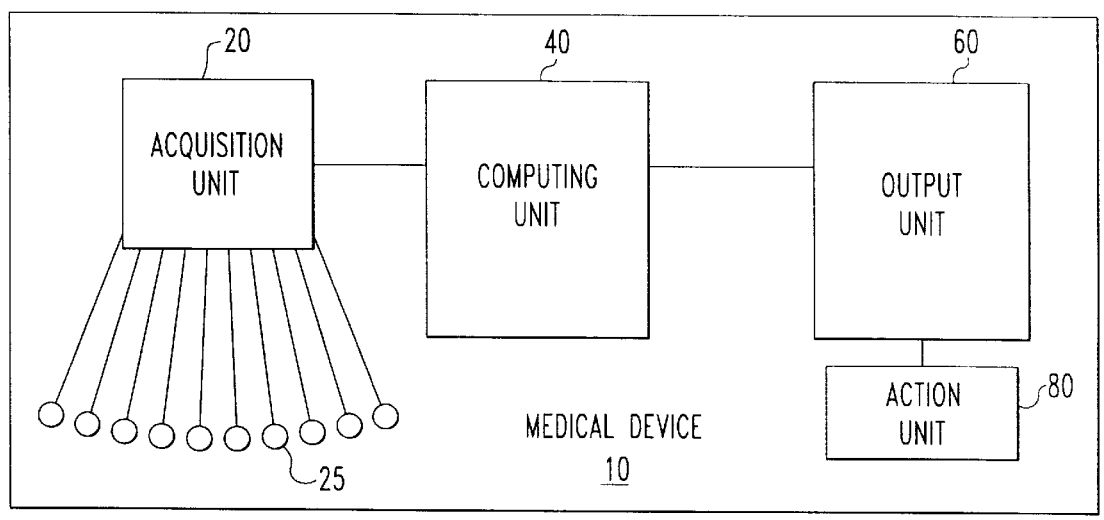
FIG. 1 is a block diagram of the medical device of the preferred embodiment of this invention.

FIG. 1 is a block diagram of a preferred embodiment of a medical device 10 of this invention. The device may include an acquisition unit 20 that may have electrodes 25 for attachment to a patient, not shown, to receive electrocardiographic data, a computing unit, an output unit 60 and an action unit 80. The acquisition unit may receive ECG data, such as an RR-series, from a recorded data source for analysis, but preferably receives the data real-time, on-line through the electrodes 25 that are connected to a patient. As used herein, patient means an animal, and most likely a human. The medical device further includes a computing unit 40 for dividing the signal from the acquisition unit into a series of time windows or segments and decomposing the signal into a plurality of components that show the most significant information about the signal. The components are indicative of the magnitude and complexity of the data for comparison and pattern recognition. The output unit 60 may include a screen to display the component signals for pattern recognition or may alternatively or additionally feed an output signal to an action unit 80 for sounding an alarm or taking appropriate preventative measures such as applying anti-arrhythmic drugs or adjusting the therapy mode.

In a preferred embodiment of this invention, the acquisition unit receives the RR-series from the patient and uses the Karhunen-Loeve Transformation (KLT) for the detection of linear and nonlinear changes in the beat-to-beat heart rate time (RR) series of different complexity to predict LTCA. KLT is an orthogonal transformation that employs a weighted combination of several basis functions to represent a signal. The basis functions are fixed, whereas KLT-coefficients vary as a function of time. The choice of KLT for detection and characterization of the changes in RR-series was related to the following properties of the transform:

minimization of the mean square error within a finite number of basis functions guarantees that no other expansion will give a lower approximation error (with respect to the mean square error);

clustering transformational properties with minimization of the entropy in terms of the average squared coefficients used in the expansion.

A minimum number of basis functions is needed to obtain a fixed reconstruction error compared to other orthogonal expansions. In contrast to the methods that use fixed-form basis functions (for example, Fourier representation), basis functions in KLT are derived from the statistics of the signal. Therefore, KLT with the same number of basis functions provides a smaller residual error than other expansions.

Assume that the pattern contains M vectors $\{x_i, i=1,2,\ldots,M\}$, and the length of each vector is equal to N points. To obtain the KLT coefficients, covariance matrix $C_x$ must be obtained. The covariance matrix $C_x$ is defined as $$C_x = E[(x-m_x)(x-m_x)^T] \quad (1)$$

where $$m_x = E[x] \quad (2)$$

is the mean vector, and E corresponds to the expected value. Equations 1 and 2 can be estimated as follows:

$$\hat{C}_x = \frac{1}{M}\sum_{i=1}^{M}(x_i - \hat{m}_x)(x_i - \hat{m}_x)^T \text{ and} \quad (3)$$

$$\hat{m}_x = \frac{1}{M}\sum_{i=1}^{M}x_i \quad (4)$$

The dimension of the mean vector is N×1, and that of the covariance matrix is N×N.

From the covariance matrix one can obtain eigenvectors $\{\psi_i, i=1,2,\ldots,N\}$ and corresponding eigenvalues $\{\lambda_i, i=1,2\ldots,N\}$. Let A be the transformation matrix whose rows are the eigenvectors of $C_x$. First eigenvector corresponds to first eigenvalue, second one corresponds to second eigenvalue and so on. Eigenvalues are arranged in decreasing order so that $\lambda_1 \geq \lambda_2 \geq \ldots \geq \lambda_N$. Then, KLT consists of a multiplying transformation matrix A by vector $(x-m_x)$:

$$\text{vector of } y_i = A(x_i - \hat{m}_x) \quad (5)$$

where $y_i$ is the KLT-coefficients in $i^{-th}$ window.

In previous works, KLT was applied for detection and classification of cardiac waveforms (QRS-complexes and ST-segments) on ECG. The optimal basis functions for QRS or ST waveforms were obtained from large training sets. KLT coefficients were used to compare individual waveforms with the set of templates and to assign the waveform to one of the classes. Because heart beat time series is nonstationary and high variable among subjects and in the same subject over different periods of time, typical waveforms or templates of RR-series cannot be determined. Therefore, in this invention the temporal, adaptive changes in KLT coefficients are used to detect and characterize the changes in RR-series. Pronounced and complex changes in the RR-series are detected by the simultaneous changes in several KLT coefficients. These combined changes in KLT coefficients have been observed to occur approximately 2 hours before the onset of LTCA in the majority of patients.

The signal is separated into consecutive windows, and an array of vectors is obtained from the series. The covariance matrix is estimated according to the equation No. 3 above, where M is the number of vectors, $x_i$ is $i^{th}$ vector, and $m_x$ is calculated as in formula No. 4. Basis functions or eigenvectors are obtained from this matrix. Since only one covariance N×N matrix (N is the window length) is generated from the signal, all eigenvectors are fixed.

EXAMPLE 1

Figure 2:
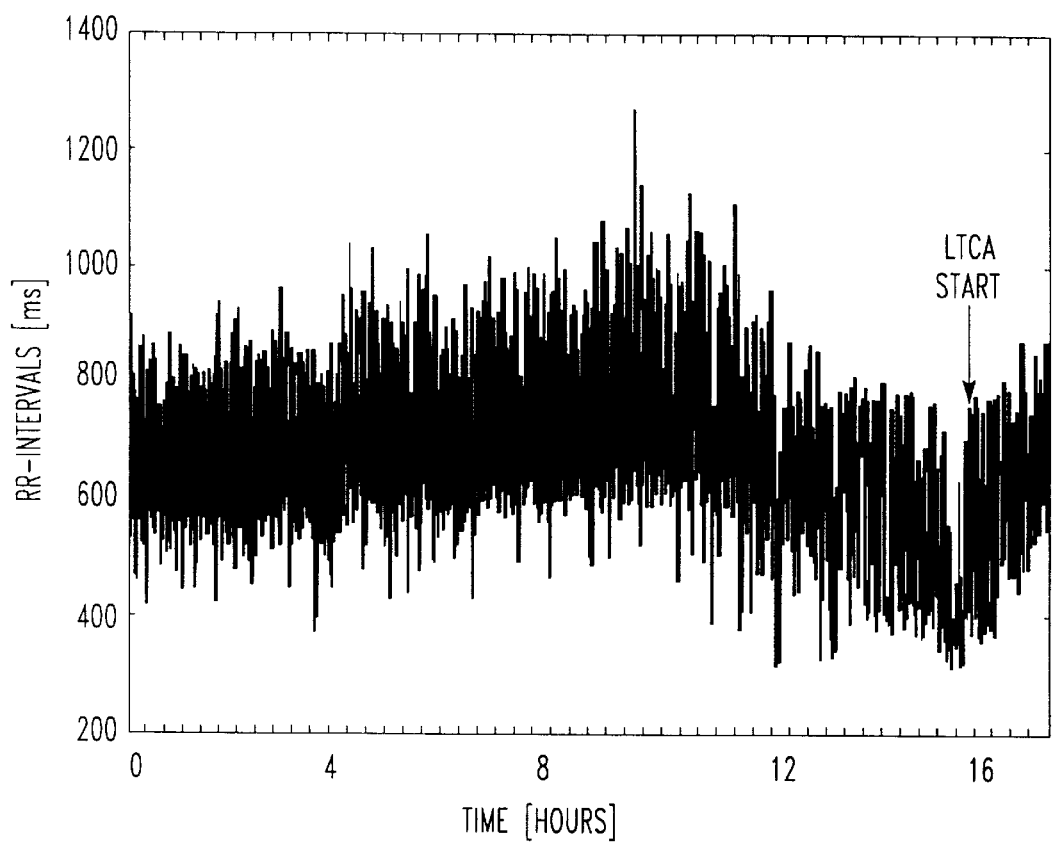
FIG. 2 is a graph of a representative RR-series.
Figure 3A:
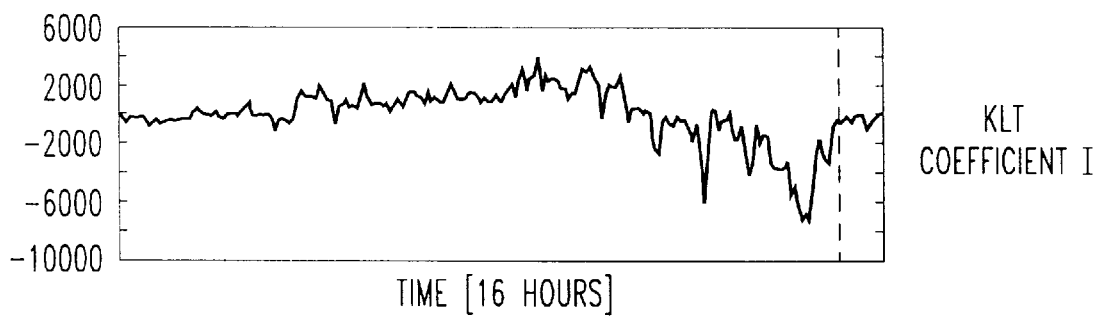
FIG. 3 shows the first six KLT-coefficients (A–F) obtained from the RR-series in FIG. 2.
Figure 3B:
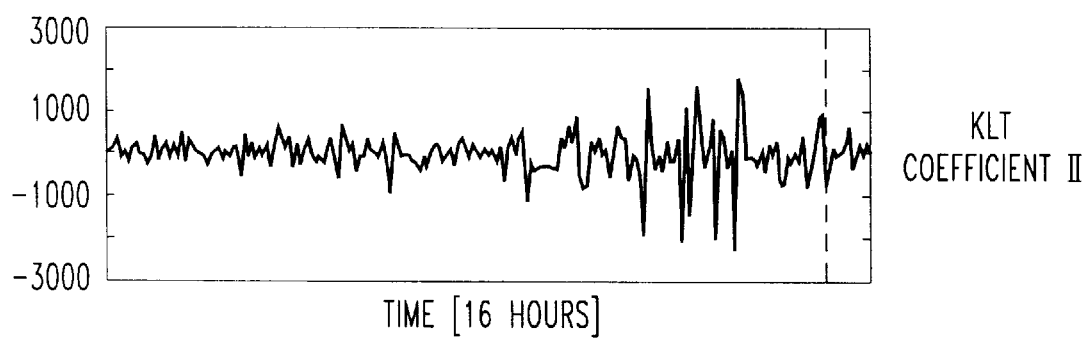
Figure 3C:
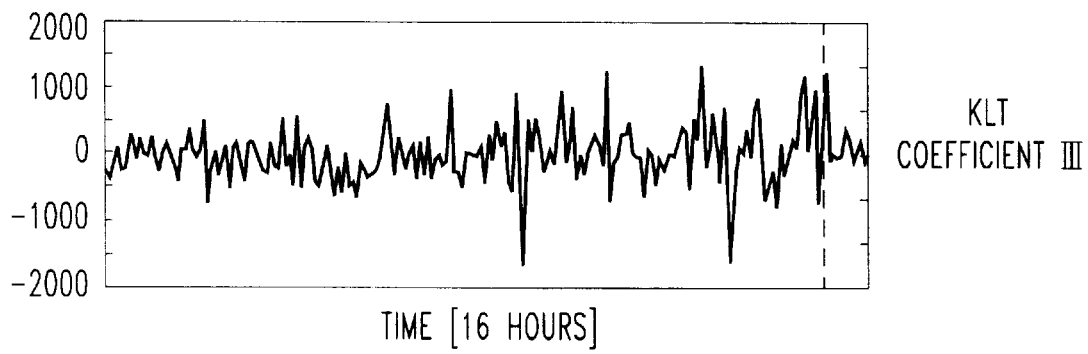
Figure 3D:
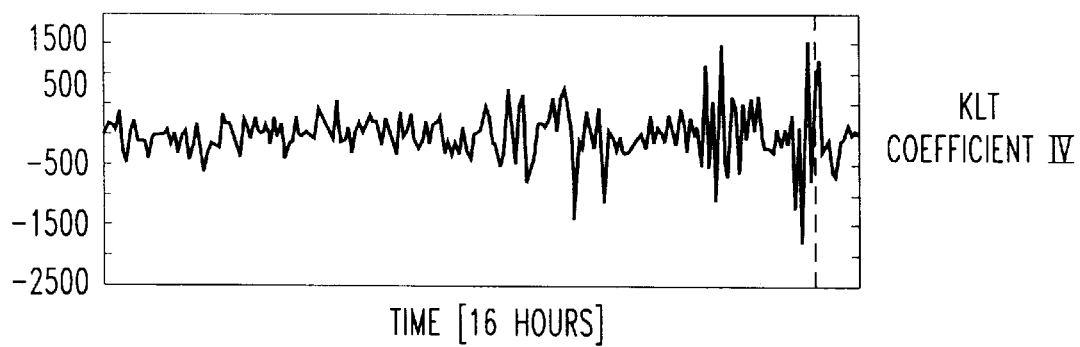
Figure 3E:
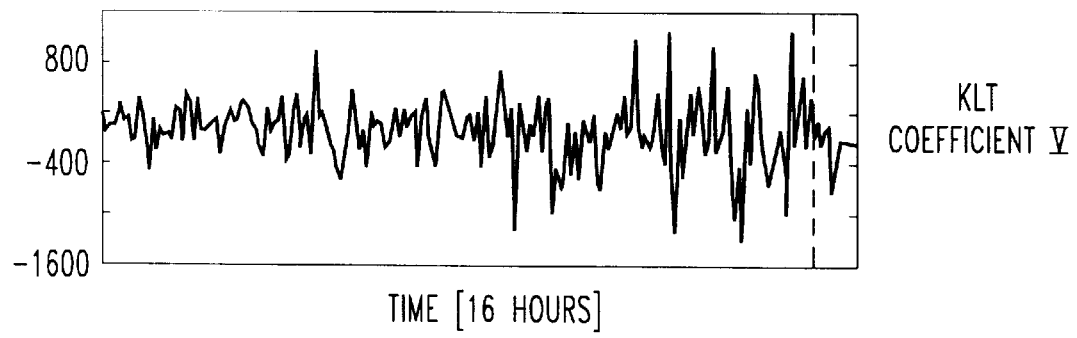
Figure 3F:
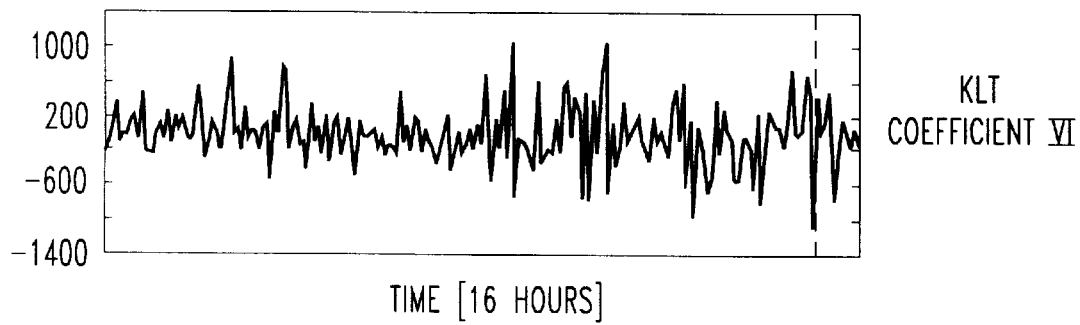
Figure 4A:
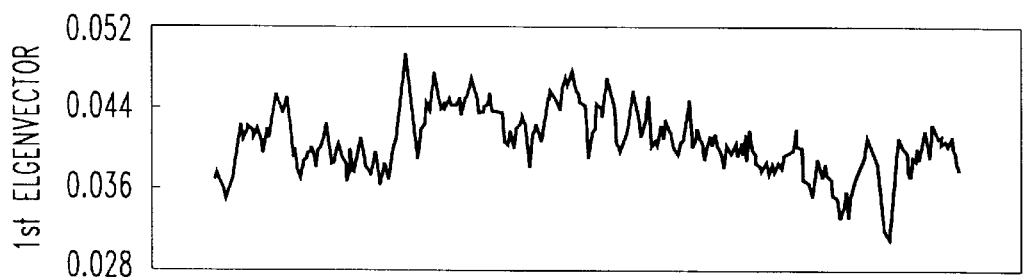
FIG. 4 shows the first six eigenvectors (A–F) obtained from the RR-series in FIG. 2.
Figure 4B:
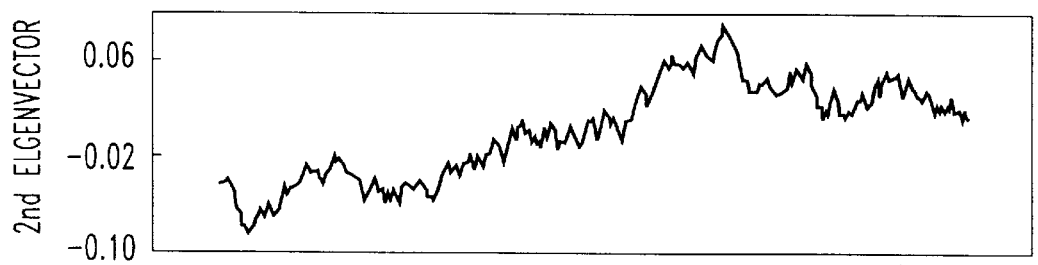
Figure 4C:
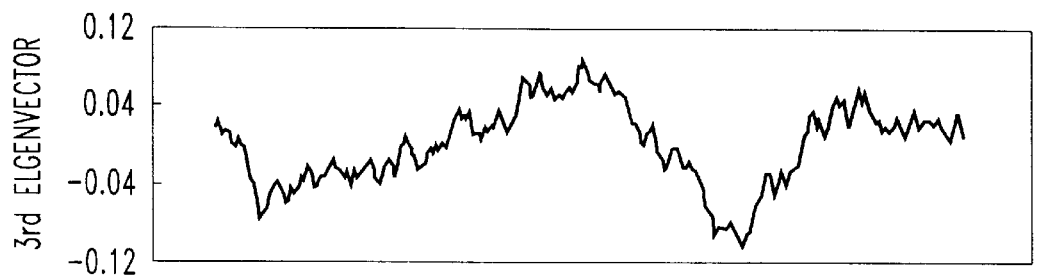
Figure 4D:
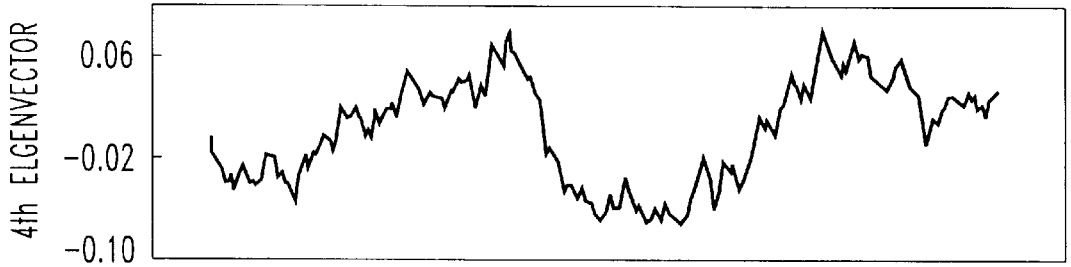
Figure 4E:
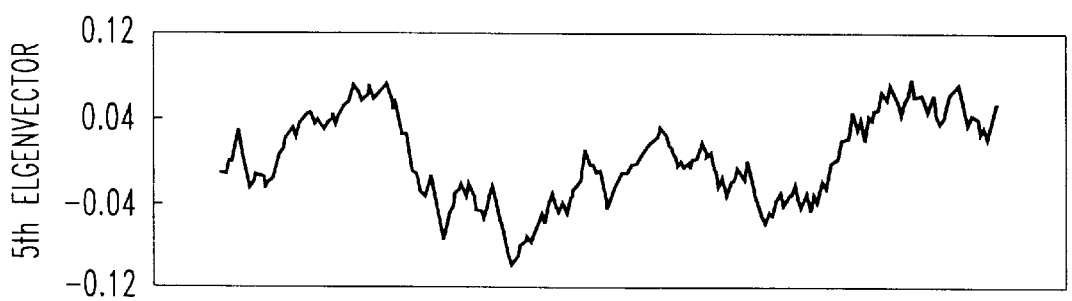
Figure 4F:
Figure 5A:
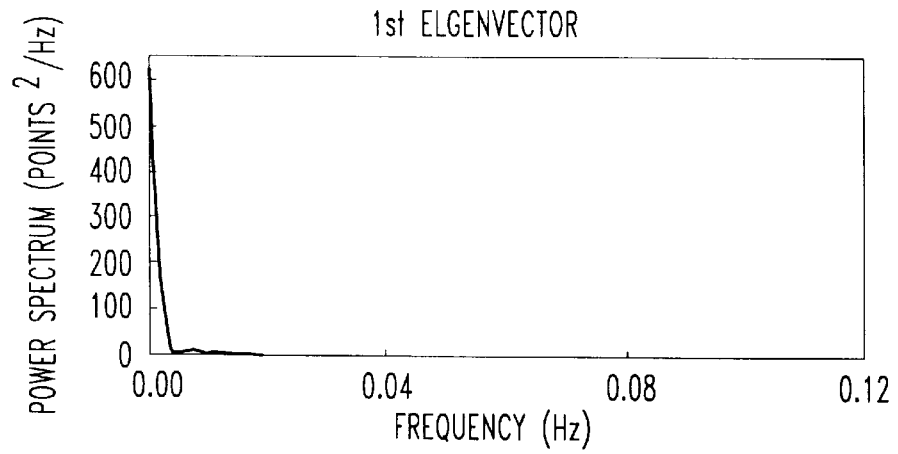
FIG. 5 shows the power spectra for the first six eigenvectors (A–F) obtained from the RR-series in FIG. 2.
Figure 5B:
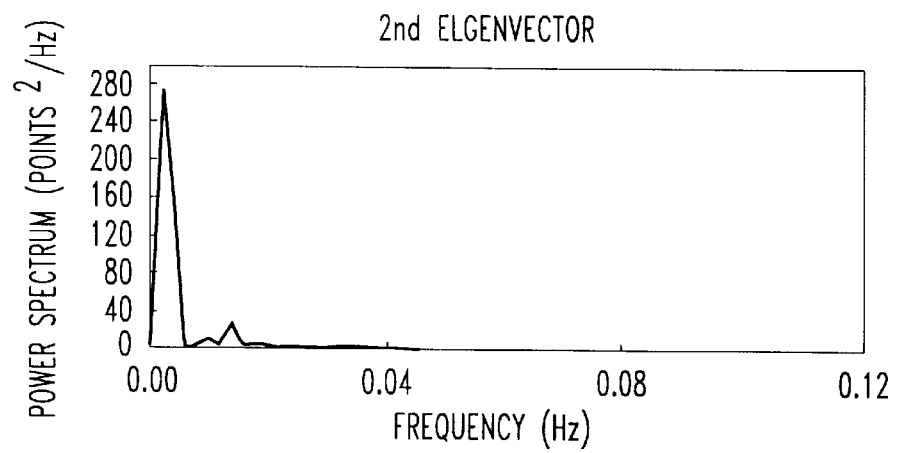
Figure 5C:
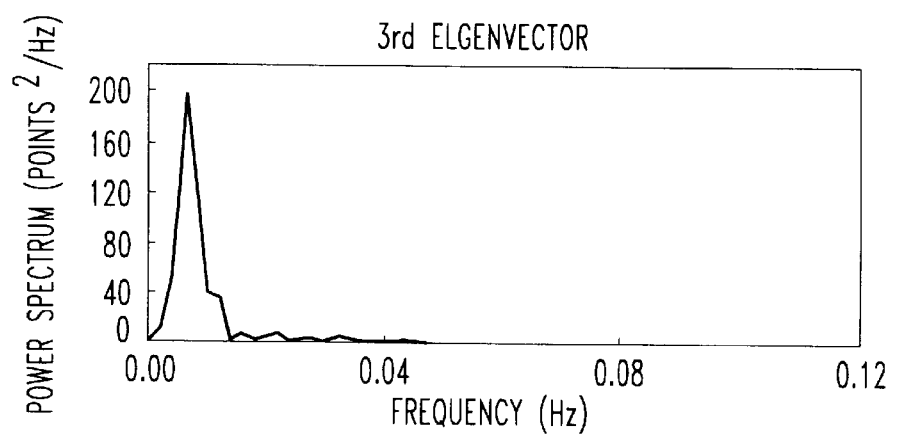
Figure 5D:
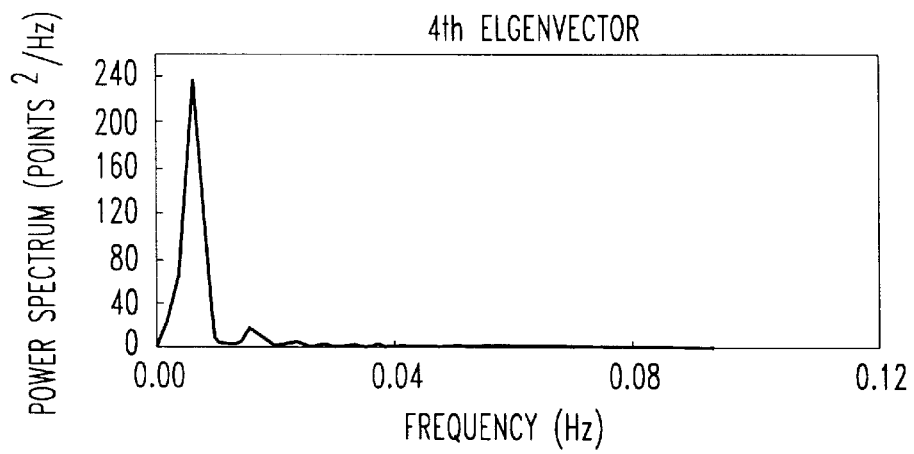
Figure 5E:
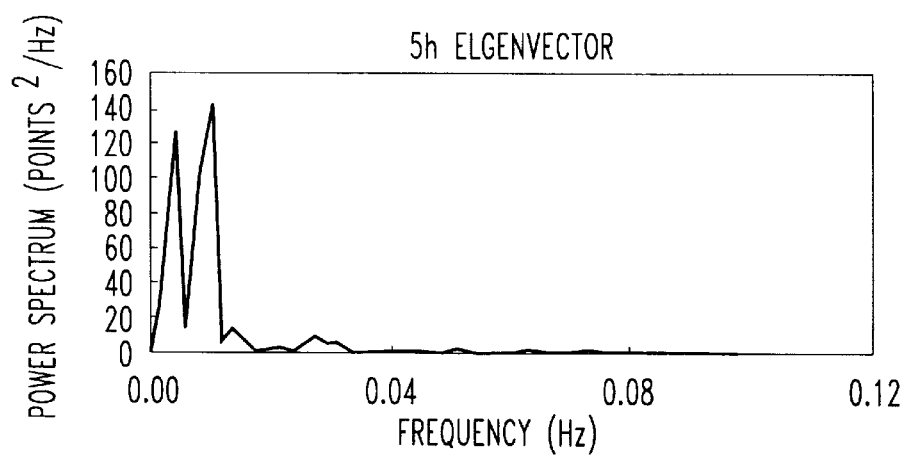
Figure 5F:
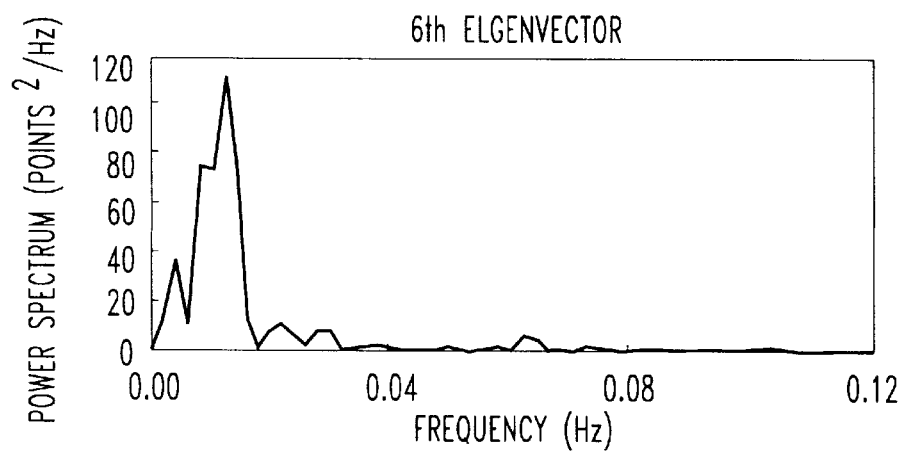
Figure 6A:
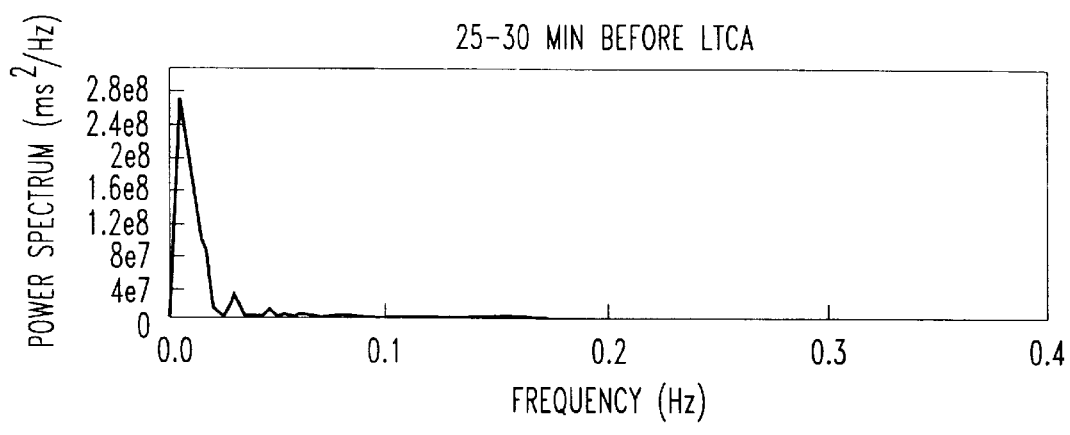
FIG. 6 shows the changes (A–F) in the power spectra of the RR-series from FIG. 2 over 30 minutes before LTCA.
Figure 6B:
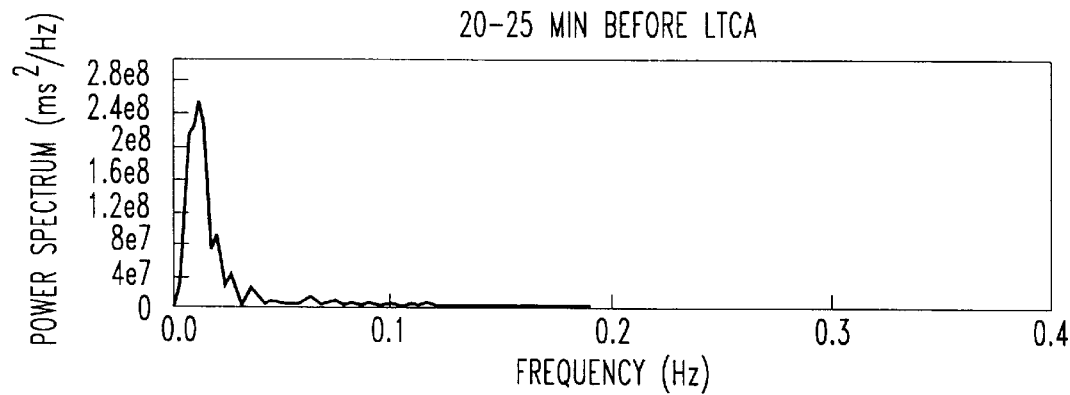
Figure 6C:
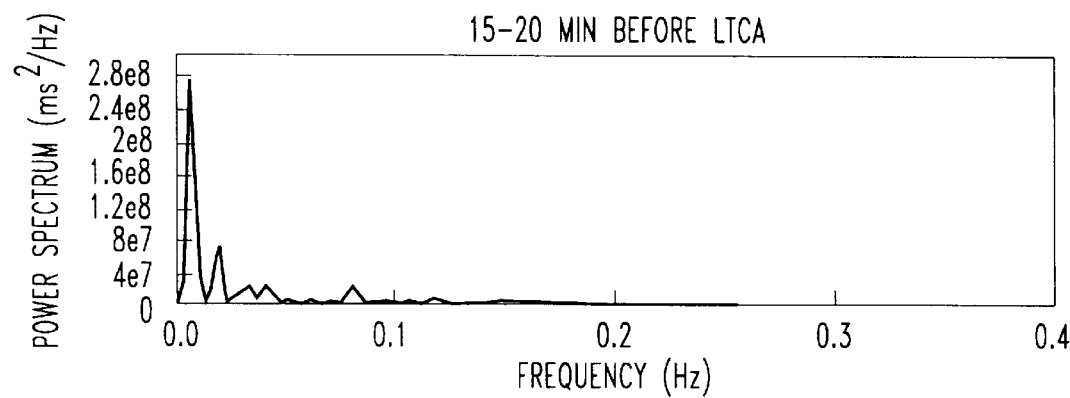
Figure 6D:
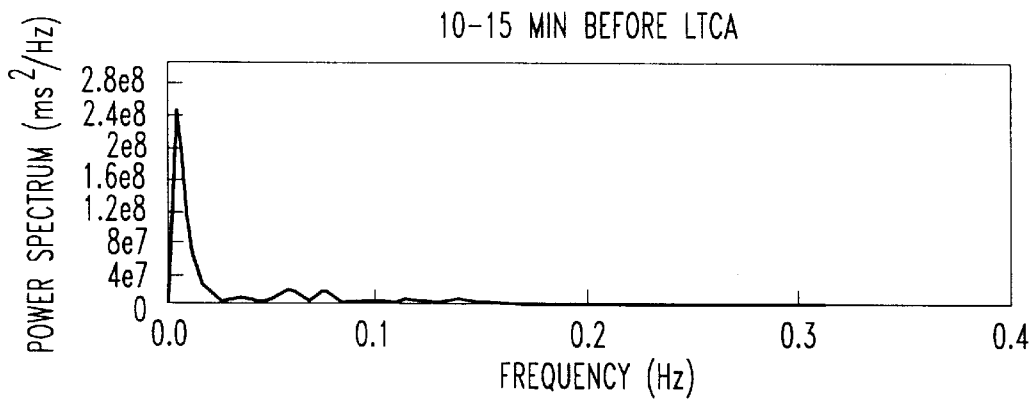
Figure 6E:
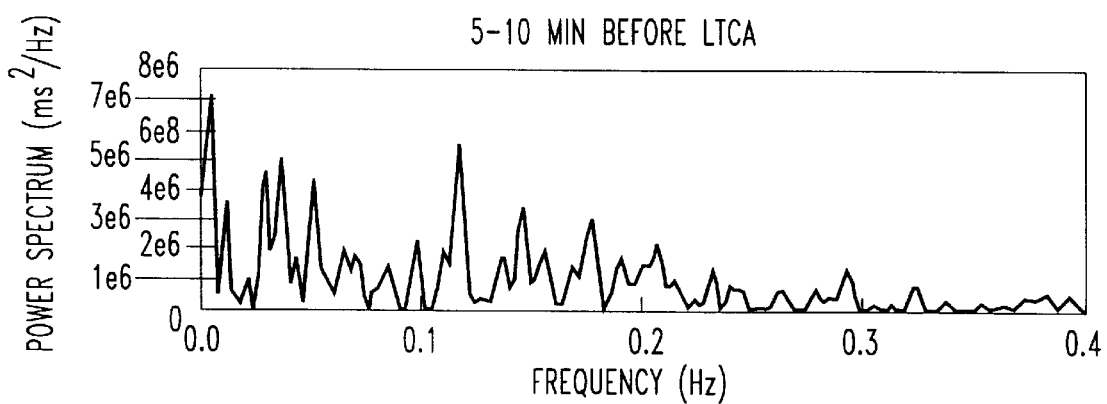
Figure 6F:
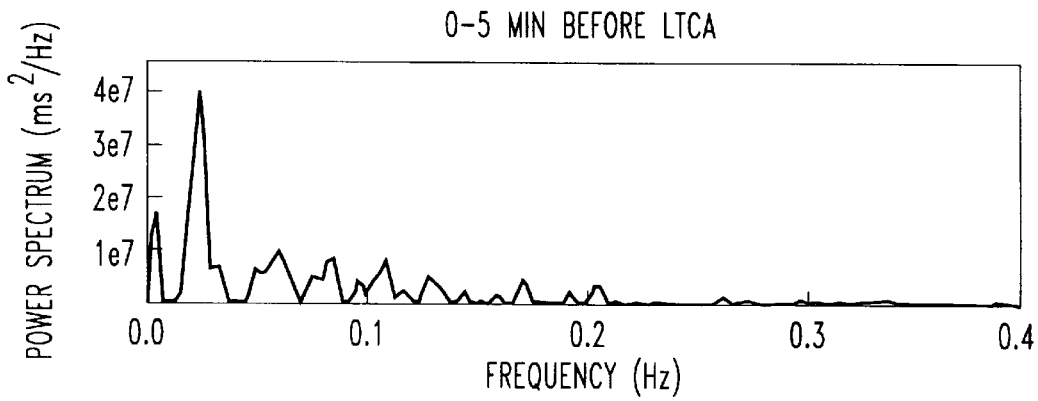
Figure 7A:
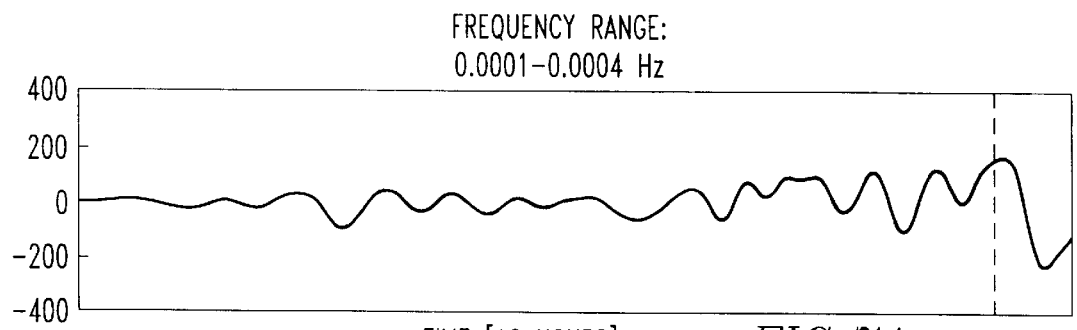
FIG. 7 shows the display of an alternative method of this invention in which the RR-series of FIG. 2 is decomposed into seven ranges (A–G).
Figure 7B:
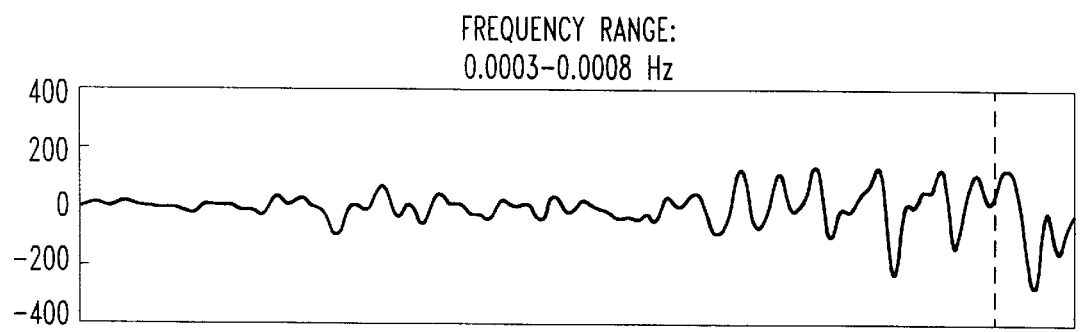
Figure 7C:
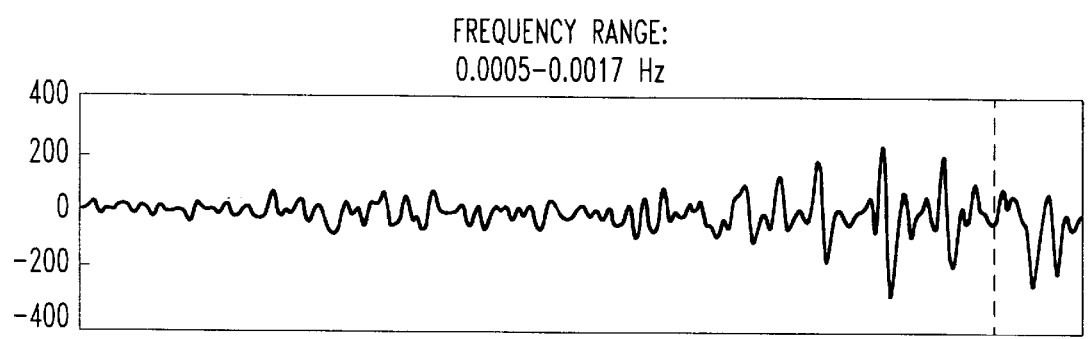
Figure 7D:
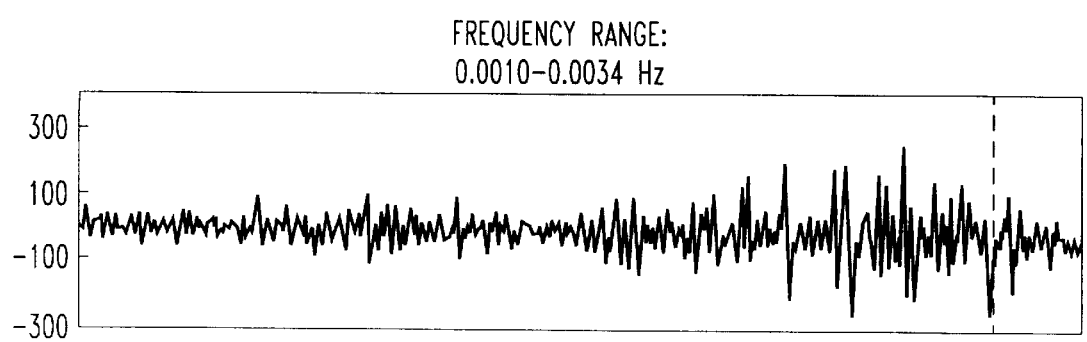
Figure 7E:
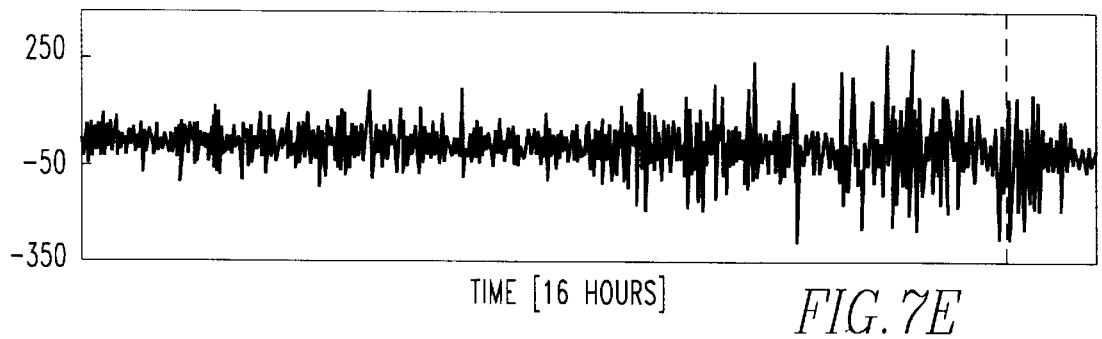
Figure 7F:
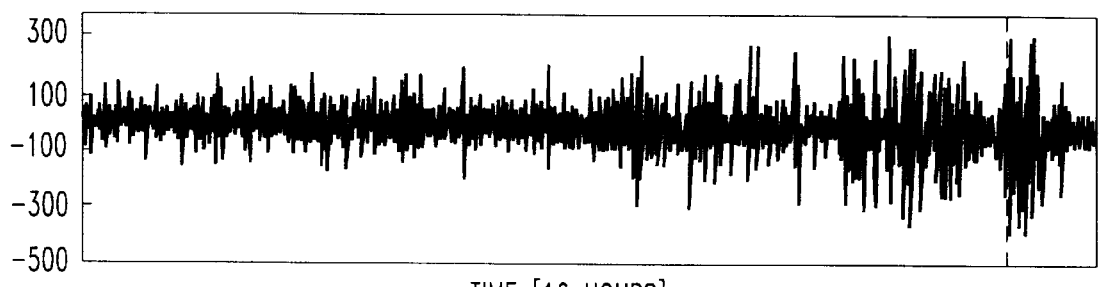
Figure 7G:
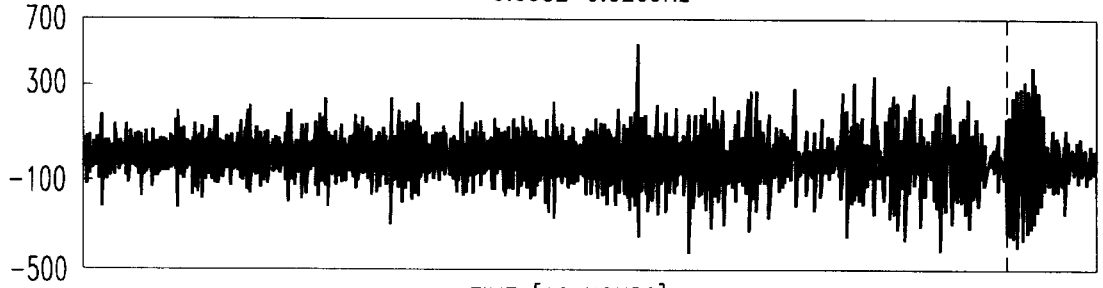
Figure 8A:
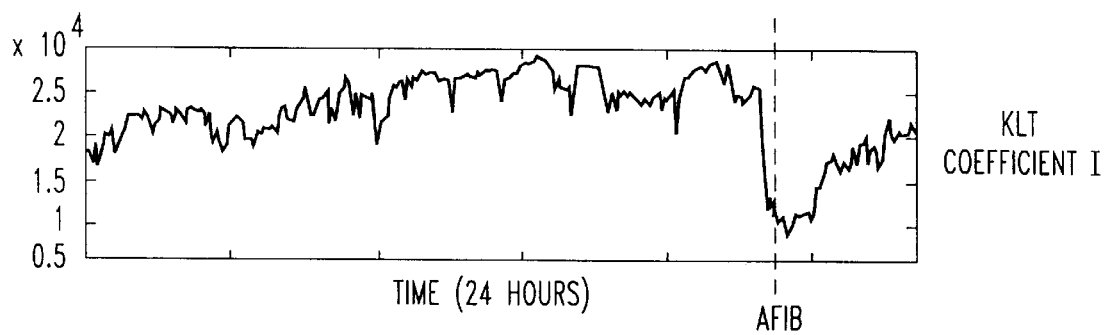
FIG. 8 is a graph of six KLT-coefficients for Example 2 of this invention.
Figure 8B:
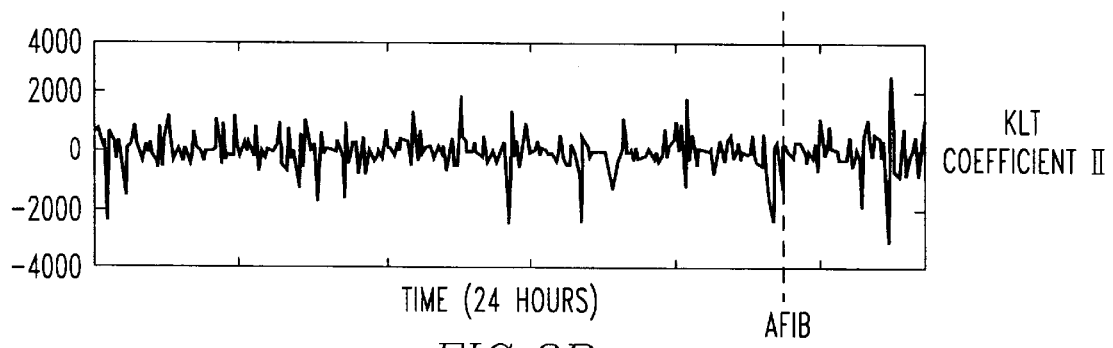
Figure 8C:
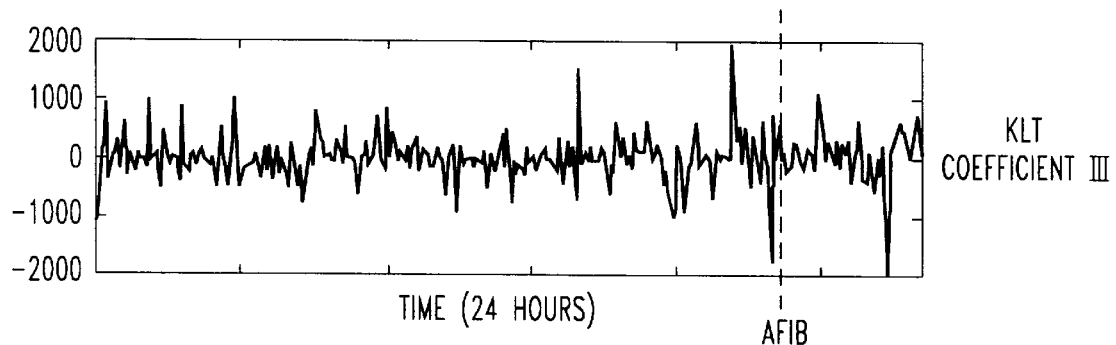
Figure 8D:
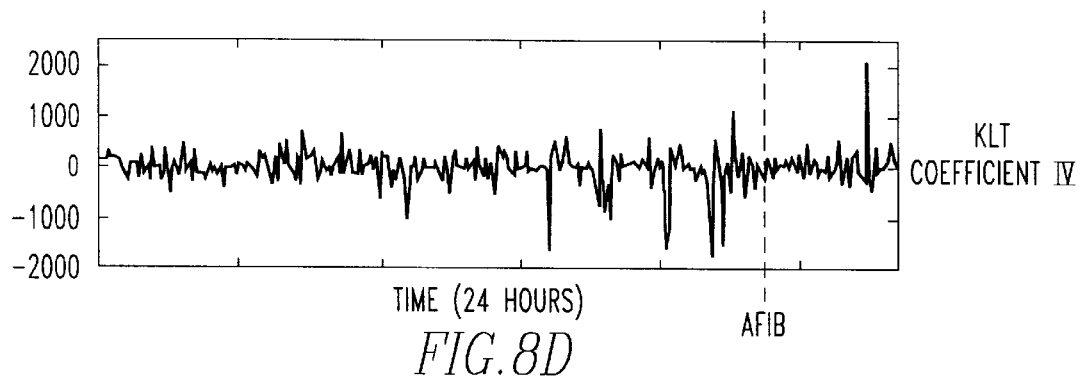
Figure 8E:
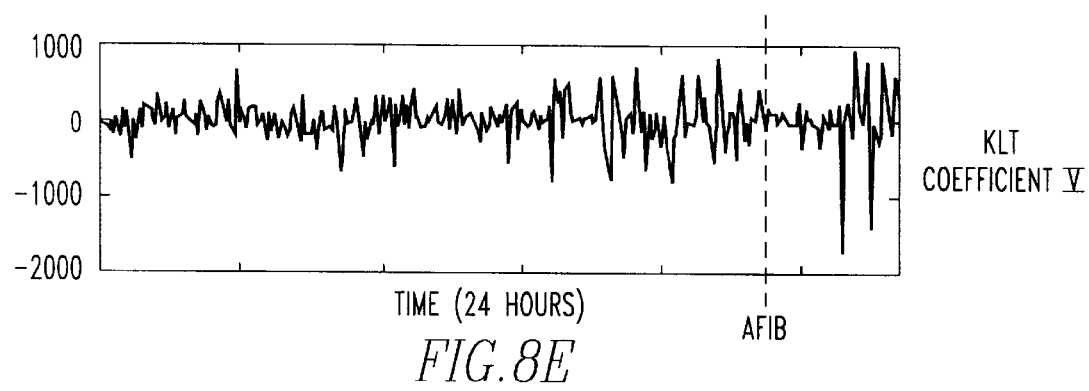
Figure 8F:
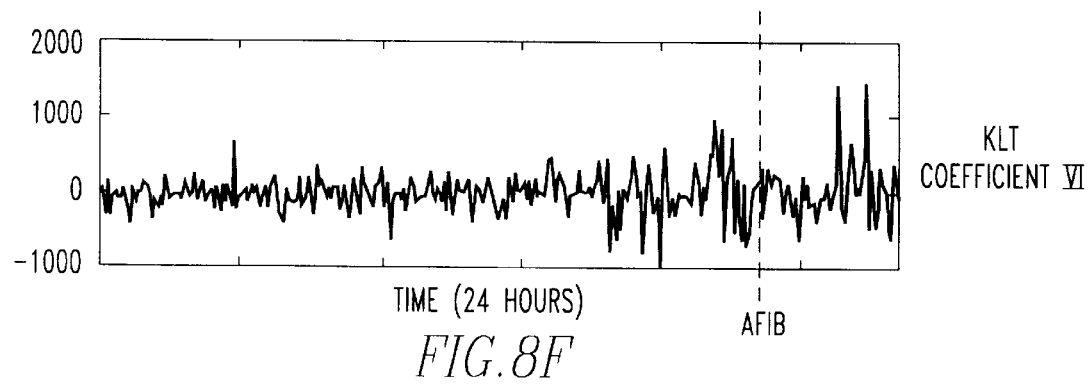

A representative example of the raw RR-series over 16 hour is shown in FIG. 2. As shown in that Figure, the raw RR-series (in milliseconds) is taken over 16 hours, and the onset time of LTCA is marked by arrow. Several types of changes in the series are seen, including slow progressive shortening of RR-intervals, abrupt quasi-periodic jumps, and changes in variance precede initiation of the event. However, the complex, multicomponent character of the changes precludes an accurate tracking of each component in the raw signal and requires application of pattern recognition techniques. The window length N is chosen as 300 seconds, and the number of vectors (windows) is 202. FIG. 3 shows the first six KLT-coefficients obtained from the RR-series in FIG. 2. The onset time of LTCA is marked by dashed line. All KLT-coefficients exhibit changes in the mean (1st coefficient) and variance (2nd–6th coefficients)

several hours before the onset of LTCA. Because the very low frequency component predominates in the signal, the series of the first KLT-coefficient tracks the envelope or time-varying mean of the signal. KLT-coefficients No. 2–6 represent components of smaller magnitude and higher frequency.

The frequency content that is associated with each KLT-coefficient can be obtained from the corresponding eigenvectors. FIG. 4 shows the first six eigenvectors (KLT basis functions) obtained from the RR-series in FIG. 2. The length of each eigenvector is 600 points.

FIG. 5 shows the power spectra of the first 6 eigenvectors obtained from the RR-series in FIG. 2. Peak frequency of the 1st eigenvector corresponds to DC (0 Hz), and it drifts progressively to higher frequencies from the 2nd to 6th eigenvector. The spectra were obtained using FFT. The first KLT-coefficient contains the lowest frequency, whereas the 6th coefficient contains the highest frequency components. Intermediate 2nd–5th KLT-coefficients represent a gradual transition from the very low to the high frequencies. Using the procedure described above, the frequency characteristics of the changes in RR-series can be obtained.

FIG. 3 (A–F) illustrates that all 6 KLT-coefficients exhibit pronounced changes several hours before the onset of LTCA. The time varying mean of the first coefficient decreases which indicates an increase in heart rate preceding the LTCA event. The mean values of the other KLT-coefficients do not change but their oscillations (variance) increase before LTCA. An increase in the mean heart rate associated with the changes in the 1st KLT-coefficient could be detected by the time domain analysis (mean and standard deviation) of RR-series. However, the complexity of the changes as indicated by the other KLT-coefficients cannot be detected by the standard time domain techniques. In the majority of patients the changes in mean heart rate alone do not predict LTCA. Furthermore, the spectral analysis cannot adequately reveal the complexity of the changes because of nonstationarity of the signal. FIG. 6 shows changes in the power spectra of the RR-series from FIG. 2 over 30 minutes before LTCA. Each spectrum was obtained from a 5-minute interval using FFT and Hanning window after subtraction of the mean (DC) from the signal. The spectra contain a number of varying frequency components and prominent very low frequency (<0.04 Hz) peaks. This obscures tracking of the characteristics changes that might predict LTCA.

Power spectra of the RR-series obtained in 6 consecutive 5-minute windows (30, 25, 20, 15, 10 and 5 minutes before the onset of LTCA) contain numerous energy components. However, the analysis is obscured by nonstationarity of the very low frequency elements which predominate the power spectra and make the complex changes in the other frequency components undetectable. Application of nonlinear methods (point correlation dimension) can demonstrate the changes in complexity of RR-series but cannot reveal the pattern, the onset time, and the magnitude of changes. This diminishes the practical value of these methods for the short-term prediction of LTCA. In contrast, analysis of the combined changes in KLT-coefficients detects the unstable period with the simultaneous changes in all 6 KLT-coefficients 2–3 hours before the onset of LTCA. In all patients, combined changes in <3 coefficients predict the event with a 100% accuracy.

Test Data

Subjects: Ambulatory 24-hour Holter ECGs from 48 subjects (age: 65±10 years) with recorded LTCA (spontaneous sustained monomorphic ventricular tachycardia) were used for validation of the method of the present invention. All subjects had structural heart disease, 82% ischemic (coronary artery disease), ejection fraction (an index of cardiac function): 34±16% (normal range is above 55%), 87% were men, none were on antiarrhythmic drugs.

Signal Processing and Data Analysis: The ECG were recorded on analog magnetic tapes and digitized at 400 Hz. QRS complexes were detected and classified on a commercial scanning system running a software customized for this purpose (Burdick Inc., Wis.) and verified by a cardiologist. Intervals between normal QRS complexes were extracted, whereas ectopic beats were excluded from the RR interval series. The time series of these RR intervals was linearly interpolated, sampled at frequency 2 Hz, and KLT of the signal was performed. The time-varying mean and variance of the first 6 KLT coefficients were analyzed over the entire 24-hour period in consecutive, nonoverlapping 5-minute time windows.

Results: In 92% of patients there was a pronounced change at least in one coefficient over 2 hours before the onset of LTCA. This shows that changes in RR-series preceding the onset of LTCA occur in the majority of patients. The changes had different frequency characteristics, had linear or nonlinear character in different subjects. Therefore, they cannot be detected by methods that track a single type of change.

In 65% of patients 2 or more coefficients changed before LTCA. This indicates that complex changes in the RR-series include several components with different time-frequency characteristics (Table 1). In 15% of patients the first KLT coefficients, which represents the time-varying mean of the signal, has a maximal variance and/or mean before the arrhythmia. In these subjects the mean and variance of RR-series can be used to detect the changes that precede LTCA. However, in the majority (77%) of patients they cannot be detected by standard linear analysis.

Changes in 4 or more KLT coefficients, which corresponded to the most complex and pronounce perturbations in the RR-series, were observed in 23% of patients. In these patients the combined changes in KLT coefficients 2 hours before LTCA predicted the event with a 100% accuracy. Changes in 3 coefficients or less had a high sensitivity (92%) but low specificity.

There were no differences between the clinical characteristics of patients with different numbers of KLT coefficients changing before the arrhythmia.

TABLE 1

Changes in KLT Coefficients 2 Hours Before LTCA

| Number of Changing Coefficients | Number of Subjects | % of Subjects |
| --- | --- | --- |
| ≧6 | 6 | 12.5 |
| ≧5 | 8 | 16.7 |
| ≧4 | 11 | 22.9 |
| ≧3 | 24 | 50 |
| ≧2 | 31 | 64.6 |
| ≧1 | 44 | 91.7 |
| ≧0 | 48 | 100 |

FIG. 7 (A–G) shows the component signal produced by an alternative method of decomposition or compression of a signal of electrocardiographic data into components that contain the most significant information about the signal. This method utilizes wavelet decomposition of the signal into a plurality of frequency ranges. As shown in FIG. 7, the RR-series from FIG. 2 is decomposed into seven frequency ranges. The onset time of LTCA is marked by the dashed line. All frequency components exhibit changes in variance several hours before the onset of LTCA. However, the frequency of the changes varies among individual patients and therefore the changes may not be exposed by the decomposition into predefined frequency ranges.

EXAMPLE 2

I. Short-term Prediction of Paroxismal Atrial Fibrillation and Atrial Flatter

Study Patients

Holter ECGs obtained from 9 patients with recorded intermittent atrial fibrillation (AFIB) were studied. In all patients, AFIB was preceded by normal (sinus rhythm). Eight patients had one episode of AFIB; one patient had 2 AFIB during the entire period of recording.

Methods

Time series of RR-inervals includin ectopic beats were generated. Karhunen-Loeve Transform was applied in 5-min windows to obtain the KL-coefficients (KLC) and eigenvectors. The first 6 KL-coefficients were selected in each patient. The coefficients reflect any changes in the RR time series. A set of thresholds was defined using the standard deviations (SD) of the coefficients. For the 1st coefficient, the threshold was defined as:

$$T=\text{mean}(1^{st}KLC)-3*SD(1^{st}KLC).$$

For all other coefficients, a range of threshold values was defined as $\pm SD$.

Using 4-hour windows, we examined the total number of the KLC that exceeded thresholds in each window before the onset of AFIB.

Results

The total number of the KLC that exceeded the thresholds increased before the onset of AFIB in most of the patients. In 5 out of 9 patients, four or more KLC exceeded the thresholds preceding the onset of AFIB. Using this method, only one false detection was encountered in the entire data set (four KLC exceeded the thresholds 12 hours before the onset of AFIB). Thus, the sensitivity of this method was 56%, and specificity was 89%. An example of successful prediction of AFIB in one patient is shown in FIG. 8. The dashed line indicates the onset of AFIB. Changes in the four KLT coefficients were detected before the onset of AFIB.

II. Pacing Stimulation Application

The stimulation can be delivered using any commercial stimulation device (for example, PACE-1A Programmable Cardiac Stimulator 4.0; Radionics, Inc., Burlington Mass.) approved for clinical studies. The stimulator will be operated in the trigger mode and appropriately timed trigger events will be provided by a computer program. Stimulus impulses will be set to EPS laboratory standards which are 2 ms rectangular pulses at twice diastolic threshold. The algorithm consists of the following steps. First, the RR-series will be obtained from ambulatory ECG and decomposed into n components (KLC) $c_1 \ldots c_n$. Second, starting from i=1, each component $c_i$ will be modified according to the average change in this component before the onset of spontaneous arrhythmia in the training set. Data from the same patient or from a group of patients can be used as a training set. Using the modified component $\tilde{C}_i$, unmodified components $c_i \ldots c_{i-1}, \ldots, c_{i+1} \ldots c_n$, and the corresponding eigenvectors, the RR-series will be reconstructed. This reconstructed sequence, which has n-1 original components and one modified component, is similar to the original RR-series but also contains the features of RR-dynamics that precede the onset of spontaneous arrhythmia. This signal will be sent to the stimulator for 2 minutes. Third, the next component $C_{i+1}$ will be modified as described above, and the signal with two modified components will be reconstructed and sent to the stimulator for 2 minutes. This procedure will be repeated adding one modified component to the acing sequence each time and thus increasing the complexity of STRRIPs protocol will last a total of 15 minutes and will be repeated during dobutamine infusion and after propranolol administraiton.

Whereas particular aspects of the method of the present invention and particular embodiments of the invention have been described for purposes of illustration, it will be appreciated by those skilled in the art that numerous variations of the details may be made without departing from the invention as described in the appended claims. This invention can be used to predict a variety of cardiac arrhythmias, including life threatening and non-life threatening arrhythmias. The invention can also be used as a diagnostic for producing pacing stimulation protocols for diagnostic testing in patients having a history or high risk of arrhythmias. It can also be used for analysis of heart rate dynamics that include ectopic (abnormal) beats.

What is claimed is:

1. A medical device for predicting cardiac arrhythmias comprising:

means for receiving data from a patient of electrocardiographic activity over a period of time (hours);

means for dividing said data into a plurality of time segments;

means for decomposing said data from each time segment into a plurality of component signals that denote the magnitude and complexity of said electrocardiographic activity in each time segment; and means for providing an output signal corresponding to each of said component signals for comparison with the component signals from the other time segments to facilitate predicting the likelihood of the occurrence of a cardiac arrhythmia.

2. A medical device as set forth in claim 1 in which said data from each segment is divided into consecutive time segments of several minutes each.

3. A medical device as set forth in claim 1 in which said means for monitoring data monitors a patient's cardiovascular data on-line, real time.

4. A medical device as set forth in claim 3 in which said cardiovascular data comprises a patient's RR-series.

5. A medical device as set forth in claim 1 in which said means for decomposing said data decomposes the data into at least two to ten component signals.

6. A medical device as set forth in claim 1 including an action unit for noting the number of component signals that exhibit substantially simultaneous changes and for causing action designed to prevent the occurrence of a cardiac arrhythmia.

7. A medical device as set forth in claim 1 which monitors predefined parameters that are used for the detection of changes in said time segments.

8. A medical device as set forth in claim 1 in which said means for decomposing said data includes means for calculating Karhunen-Loeve Transform (KLT) coefficients.

9. A medical device as set forth in claim 1 which includes means for comparing the component signals from said time segments for pattern recognition of changes that are predictive of a life threatening cardiac arrhythmia.

10. A cardiac rhythm monitoring system for predicting probability of a patient having a cardiac arrhythmia comprising:
  means for monitoring a patient's RR-series of the intervals between heart beats;
  means for characterizing said RR-series using Karhunen-Loeve Transform (KLT) and generate KLT-coefficients indicative of both linear and nonlinear changes in the RR-series; and
  means for determining the magnitude of said changes in the RR-series by using the time varying mean and variance of said KLT-coefficients and determining the complexity of said changes by calculating the number of KLT-coefficients that exhibit substantially simultaneous changes.

11. A system as set forth in claim 10 which includes means for displaying said KLT-coefficients to be read by medical personnel.

12. A system as set forth in claim 10 that includes means for dividing said RR-series during monitoring of a patient into consecutive time windows, and said changes in the RR-series provide a comparison of the signals in said time windows.

13. A system as set forth in claim 12 which includes means for calculating of KLT-eigenvectors based on said RR-series, spectral analysis of said eigenvectors, multiplication of their frequency representations by the corresponding KLT-coefficients in each time window, summing the products of said multiplication to obtain an approximate frequency representation (AFR) of the signal in each time window, and subtracting the AFR from the preceding time window to provide frequency characteristics of change in said RR-series.

14. A system as set forth in claim 10 in which KLT-coefficients are calculated by the following formula:

$$\hat{C}_x = \frac{1}{M} \sum_{i=1}^{N} (x_i - \hat{m}_x)(x_i - \hat{m}_x)^T$$

$$\hat{m}_x = \frac{1}{M} \sum_{i=1}^{M} x_i$$

$$y = A(x - m_x)$$

in which
  $C_x$=covariance matrix
  M=number of vectors in the pattern
N=length of vector
  $x_i$=vectors
  $m_x$=the mean vector
  $y_i$=vector of KLT-coefficients in the window.

15. A medical device for monitoring a patient's electrocardiographic data for predictive signs of increased risk of the occurrence of cardiac arrhythmia comprising:
  cardiac rhythm monitoring means for monitoring an RR-series of the intervals between a patient's heart beats;
  computer means for dividing said RR-series into consecutive, nonoverlapping time windows of preselected duration and converting said RR-series into Karhunen-Loeve Transformation (KLT) coefficients that vary as a function of time; and
  means for displaying said KLT-coefficients.

16. A medical device as set forth in claim 15 that includes an action unit for causing appropriate preventative actions.

17. A medical device as set forth in claim 15 which includes means for calculating KLT-eigenvectors based on said RR-series, spectral analysis of said eigenvectors, multiplication of their frequency representations by the corresponding KLT-coefficients in each time window, summing the products of said multiplication to obtain an approximate frequency representation (AFR) of the signal in each time window and subtracting the AFR from the proceeding time window to provide frequency characteristics of changes in said RR-series.

18. A medical device as set forth in claim 15 that is in the form of a cardiac rhythm monitoring device for hospital use.

19. A medical device as set forth in claim 15 that is suitable for out-of-hospital use.

20. A medical device as set forth in claim 15 that comprises an automatic external defibrillator.

21. A medical device as set forth in claim 15 that comprises a pacemaker.

22. A medical device as set forth in claim 15 that comprises a system for diagnostic ECG processing and analysis.

23. A medical device for predicting LTCA comprising means for decomposing a signal of electrocardiographic data into a plurality of elements, which contain the most significant information about the signal and tracking the changes in said elements.

24. A medical device as set forth in claim 23 that includes means for causing appropriate action to prevent a LTCA.

25. A method for predicting the risk of a patient having a cardiac arrhythmia comprising:
  continuously monitoring a patient's cardiac rhythm;
  generating an RR-series of cardiac rhythm, said RR-series comprising the intervals between heart beats in consecutive time windows;
  calculating KLT-coefficients from said RR-series, which KLT-coefficients vary as a function of time to show the magnitude and complexity of changes in said RR-series between time windows;
  displaying said KLT-coefficients; and
  reading said KLT-coefficients to predict the probability of the patient having a cardiac arrhythmia.

* * * * *

UNITED STATES PATENT AND TRADEMARK OFFICE
CERTIFICATE OF CORRECTION

PATENT NO.  : 6,308,094 B1
DATED       : October 23, 2001
INVENTOR(S) : Vladimir Shusterman et al.

It is certified that error appears in the above-identified patent and that said Letters Patent is hereby corrected as shown below:

Title page,
OTHER PUBLICATIONS, under Laguna et al., last sentence should read -- vol. 28 -- rather than "vol. 29".

Column 6,
Line 14, "$\{\Psi_i, =1,2,,,,N\}$" should read -- $\{\Psi_i, i=1,2\ldots,N\}$ --.
Line 19, in each instance where "$\geqq$" is indicated, it should read -- $\geq$ --.

Column 7,
Line 61, "<3" should read -- >3 --.

Column 10,
Line 3, "$\hat{\tilde{C}_i}$" should read -- $\tilde{C}_i$ --

Column 11,
Line 45, the section of the equation reading "$\sum_{i=1}^{N}$", should read -- $\sum_{i=1}^{M}$ --.

Signed and Sealed this

Twenty-third Day of April, 2002

Attest:

*Attesting Officer*

JAMES E. ROGAN
*Director of the United States Patent and Trademark Office*